United States Patent [19]

Lin et al.

[11] Patent Number: 5,385,725
[45] Date of Patent: Jan. 31, 1995

[54] ECHO CONTRAST AGENT FOR LEFT HEART OPACIFICATION AND METHOD OF USING THE SAME

[75] Inventors: Shoa-Lin Lin, Kaohsiung; Chung-Yuan Mou, Taipei, both of Taiwan, Prov. of China

[73] Assignee: National Science Council, Taipei, Taiwan, Prov. of China

[21] Appl. No.: 225,534

[22] Filed: Apr. 11, 1994

Related U.S. Application Data

[62] Division of Ser. No. 919,902, Jul. 27, 1992, Pat. No. 5,302,372.

[51] Int. Cl.⁶ ............................................. A61B 8/00
[52] U.S. Cl. .................................. 424/9; 128/660.01; 128/662.02
[58] Field of Search ............... 424/9, 450; 128/660.01, 128/662.02

[56] References Cited

U.S. PATENT DOCUMENTS

| | | | |
|---|---|---|---|
| 4,466,442 | 8/1984 | Hilmann et al. | 128/662.07 |
| 4,957,656 | 9/1990 | Cerny et al. | 424/9 |

FOREIGN PATENT DOCUMENTS 131540  1/1985  European Pat. Off. .

OTHER PUBLICATIONS

Feinstein et al, J. Am. Coll. Cardiol., vol. 16 (1990) pp. 316–324.
Smith et al, J. Am. Coll. Cardiol., vol. 13 (1989) pp. 1622–1628.
Berwing et al, Am. Heart J., vol. 115 (1988) pp. 399–408.
Lin et al, Paper presented at 63rd Sci. Sessions of the Am. Heart Asso. (Dec. 13, 1990).

*Primary Examiner*—Richard L. Raymond
*Attorney, Agent, or Firm*—W. Wayne Liauh

[57] ABSTRACT

An echo contrast agent for use in echocardiography is disclosed which can be introduced into the body through peripheral venous injection to opacify left ventricle. The echo agent to be injected into the body contains a plurality of gas-in-liquid microbubbles which are smaller than red blood cells and can therefore traverse the pulmonary circulation to reach the left ventricle in substantial quantity to effectuate opacification thereof. The echo contrast agent disclosed in this invention contains: (a) an aqueous solution containing 0.40–0.60 grams of albumin and 4.0–10.0 grams of glucose per 10 ml solution mixed with (b) glycerin. The ratio between (b) and (a) should be no less than 0.050. A method for preparing this echo contrast agent was also disclosed.

7 Claims, 12 Drawing Sheets

ECHO CONTRAST AGENT FOR LEFT HEART OPACIFICATION AND METHOD OF USING THE SAME

This is a divisional application of application Ser. No. 07/919,902, filed Jul. 27, 1992, now U.S. Pat. No. 5,302,372, issued Apr. 12, 1994.

BACKGROUND OF THE INVENTION

This invention relates to an improved echo contrast agent for ultrasound echocardiography. More particularly, this invention relates to an improved echo contrast agent for use in ultrasonic echocardiography that can be introduced into the body through peripheral venous injection to opacify the left ventricle.

The use of echo contrast agent in ultrasound echo cardiography was introduced by Dr. Gramiak and his coworkers at the University of Rochester. Their initial work was published in an article entitled "Ultrasound cardiography: contrast studies in anatomy and function," *Radiology*, 92:929 (1969). When an ultrasonic beam strikes a surface or traverses a tissue interface, part of the energy is absorbed, part of the energy is reflected, and another part of the beam passes through the material. The returning pulses, caused by reflected waves, are displayed on an oscilloscope and recorded. In their studies, Dr. Gramiak et al. found that the intracardiac injection of indocyanine green dye produced a cloud of echoes on the echocardiogram. They attributed this contrast effect to the microbubbles that were suspended in the indocyanine green solution prior to injection. Since then indocyanine green dye has become standard contrast agent in ultrasound echocardiography.

Other contrast agents, such as saline, 5% dextrose in water, carbon dioxide gas, hydrogen peroxide, and even the patient's blood, have been used by many echocardiographers. Other contrast agents are discussed in a book entitled "Contrast Echocardiography" edited by R. S. Meltzer and J. Roelandt. Its content is incorporated by reference. In clinic studies, the contrast agent must be introduced via a cardiac catheter injection into the ascending aorta or the coronary arteries. Such a practice requires a highly skillful person to implement. It also suffers the risk of being injected into the body, and the need of a cardiac catheter placement. For clinic purposes, it is desirable to have an echo contrast agent that can be introduced into the body through peripheral venous injection. Such an echo contrast agent must also be able to traverse the pulmonary circulation and enhance the myocardial image during echocardiography.

In order to traverse the pulmonary circulation, the contrast agent must be able to generate microbubbles that are very small in volume and stable and will not partially or totally obstruct capillary blood flow. The microbubbles so generated must be able to traverse the pulmonary circulation without significant loss so that they can arrive at the left ventricle in substantial concentration to enhance the opacification thereof during echocardiography.

As mentioned hereinbefore, although there are quite a few echo contrast agents that are available for echocardiography, most of them cannot be introduced into the body via peripheral venous injection and are not capable of traversing the pulmonary circulation. Three echo contrast agents reported in the literature that can traverse the pulmonary circulation are described below:

(1) Albunex: This is an albumin-containing powder. Its exact composition has not been made public. It has been evaluated by researchers at several medical research centers; however, it is relatively expensive and is not yet commercially available. See *J. of American College of Cardiology*, Vol. 16, Nov. 2, 1990, pp. 316–324.

(2) SHU-508: This is a monosaccharide contrast agent, made by Schenng Berlex Lab. The composition of this experimental agent has not been published. See *J. of American College of Cardiology*, Vol. 13, Nov. 7, 1989, pp. 1622–8.

(3) Gelifundal and intralipid solution: This agent has been used only at medical research center; it requires a dosage of at least 28 ml to be effective. See *American Heart Journal*, 1988, pp. 399–407.

SUMMARY OF THE INVENTION

The primary object of this invention is to develop an echo contrast agent to enhance the left ventricular opacification during echocardiography. More particularly, the primary object of this invention is to develop an improved echo contrast agent for use in ultrasound echocardio-graphy that can be introduced into the body and traverse the pulmonary circulation via peripheral venous injection to opacify the left ventricle. One of the main advantages of this invention is that the microbubbles generated with the echo contrast agent of this invention have a diameter smaller than that of a red blood cell. Another advantage of this invention is that the echo contrast agent disclosed in this invention requires very inexpensive raw materials.

The echo contrast agent of this invention was developed as a result of numerous experimental studies. The preferred composition of this invention contains: (a) an aqueous solution containing 0.40–0.60 grams of albumin and 4.0–10.0 grams of glucose per 10 ml solution mixed with (b) glycerin. The ratio between (b) and (a) should be no less than 0.050. The mixture solution is then sonicated with ultrasound to form an echo contrast agent containing microbubbles that are capable of being injected into the body via peripheral venous injection to effectuate the opacification of the left ventricle during ultrasound echocardiography.

The echo contrast agent of this invention has the following advantages:

(1) it can be introduced into the body via peripheral venous injection and traverse the pulmonary circulation without significant loss to opacify the left ventricle during ultrasonic echocardiography;
(2) it is inexpensive;
(3) it will not cause blood pressure to decrease during or after injection; and
(4) it is nontoxic and does not cause serious side effect.

Figure 1:
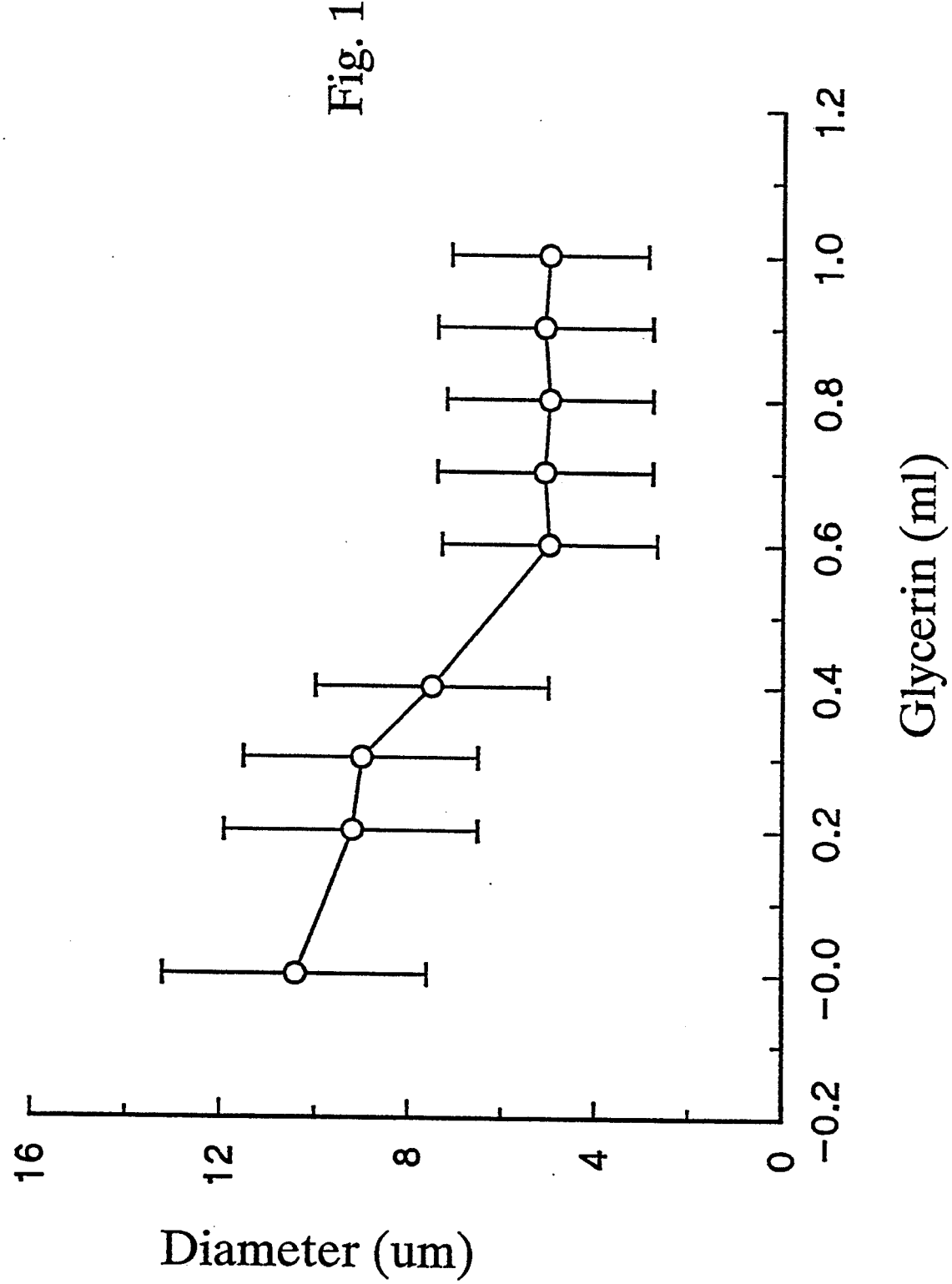
FIG. 1 is a plot of the mean diameter of the microbubbles generated from the echo contrast agent of this invention vs. glycerin concentration.

DETAILED DESCRIPTION OF PREFERRED EMBODIMENT (A) Preparation of echo contrast agent:

The first step in making the echo contrast agent of this invention was to prepare an aqueous albumin-glucose solution by first adding 50 grams of dry glucose powder into 50 ml of distilled water. The solution was heated to dissolve all the glucose powder. Then 5 grams of a commercially available human albumin (manufactured by Institute of Merieux in Lyon, France) was added to the glucose solution. Finally additional distilled water was added to bring the total volume of the aqueous albumin-glucose solution to 100 ml. The solution was again stirred to facilitate total dissolution.

The second step was to add glycerin, at a volume ratio of no less than 0.050 of the albumin-glucose solution, preferably at a ratio of about 0.060, to the albumin-glucose solution prepared according to the above-mentioned procedure. After the glycerin was settled to the bottom, the solution was sonicated.

In one embodiment, 10 ml of the albumin-glucose solution was taken from the above-prepared albumin-glucose solution and added therein 0.60 ml of glycerin. After the glycerin was settled to the bottom of the solution, it was sonicated using a Heat System sonicator (Model M-375) having a 0.5-inch diameter horn for 30 seconds at 20 KHz to generate microbubbles. After sonication, the solution was separated into three layers. The top layer was an air-liquid mixture containing larger bubbles, the middle layer was also an air-liquid mixture but containing smaller bubbles, and the bottom layer was a liquid layer. The echo contrast agent of this invention that was used for subsequent injection was obtained from the middle layer by using a syringe to quickly remove the middle layer from the mixture solution.

(B) Measurement of microbubble diameter:

After the middle layer was quickly removed from the solution with a syringe, one drop of the air-liquid mixture from the middle layer was sampled and placed onto a microscope slide which was then covered with a standard sized covertip. The sample drop sandwiched between the two glass plates was immediately placed under a microscope for observation. A videocamera was used to record the observations into high quality videotapes. The glass plates were moved around to allow for the observation of microbubbles from different regions under the microscope. A micrometer, Model MBM-11100 made by Nikon, was used to provide standardization for the quantification of the microbubble size. A total of 200 microbubbles from four different viewing regions were measured using a personal computer and with the aid of the micrometer. Their mean value of the 200 microbubbles was then calculated. In each viewing region, 50 microbubbles were selected on a continuous basis for measurement. The following are examples showing how the diameter of the microbubbles varied with the composition of the echo contrast agent of this invention. As discussed hereinabove, all the microbubbles were obtained from the middle layer.

(C) Discussion of Test Results:

Example 1: (Relationship between the microbubble diameter and the glycerin proportion)

FIG. 1 shows the microbubble diameter as a function of the volume of glycerin in a sonicated solution that contains 5.0 grams of glucose and 0.50 grams of human albumin in a 10 ml solution. The mean values, which were taken from a total of 200 observations in a procedure mentioned hereinabove, are shown as circles. Vertical error bars were also shown to describe the range of variations in the microbubble diameters.

FIG. 1 indicates that the diameter of the microbubbles decreased sharply when the volume of glycerin in the 10 ml final solution was greater than 0.6 ml (or 0.75 grams). Further increase in glycerin volume did not result in decrease in microbubble diameter.

Example 2: (Relationship between microbubble diameter and the glucose concentration)

Figure 2:
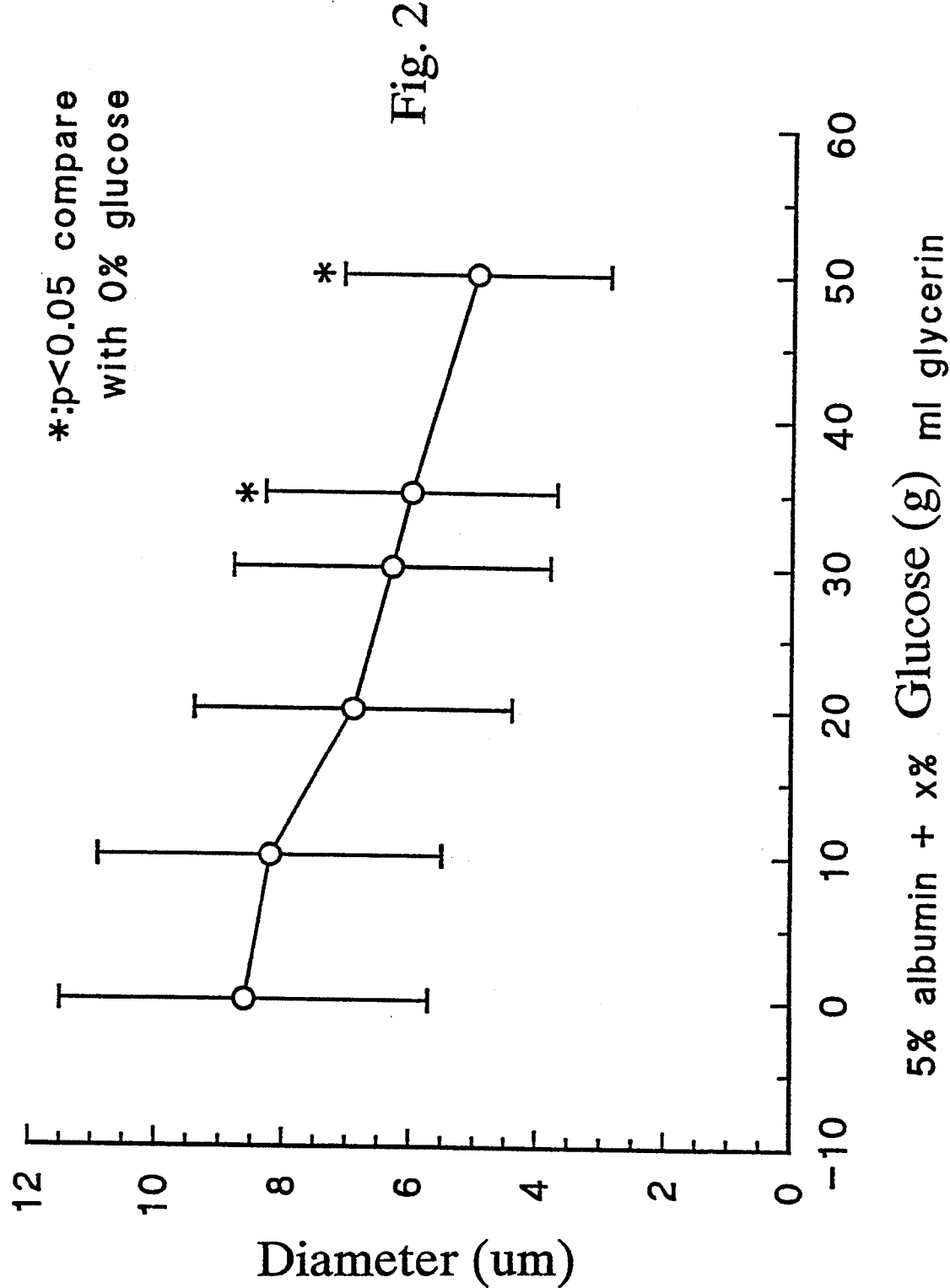
FIG. 2 is a plot of the mean diameter of the microbubbles generated from the echo contrast agent of this invention vs. glucose concentration.

FIG. 2 shows the microbubble diameter as a function of the proportion of glucose in a sonicated solution that contained 0.50 grams of albumin in 10 ml solution and with the addition of 0.6 ml glycerin. Similar to FIG. 1, the circles represent mean microbubble diameters and the ranges of measurements are indicated as vertical error bars. It can be seen that the optimum content of glucose is 5.0 grams in 10 ml of the aqueous albumin-glucose solution. Such a solution resulted in microbubbles having the smallest mean diameter.

Example 3: (Animal Experiments)

(1) Method:

(a) Experimental preparation: The experiment was performed on eight mongrel dogs weighing 14–22 kg (mean 18.6 kg). After the animals were sedated with intramuscular injections of Katamin (at 10–13 mg/kg), they were cannulated with an endotracheal tube and ventilated artificially using room air with the aid of a Harvard ventilator. The end expiratory $CO_2$ concentration was maintained at 3.5–4.5%. Anesthesia was maintained by intravenous injection of alpha-chloralose (10–30 mg/Kg) and urethane (200–400 mg/Kg). A 6F side-armed catheter was inserted into the femoral artery and interfaced with a multichannel recording system (Gould Interface 4600 and Gould ES 1000 recorder) for monitoring and recording the arterial pressure. The femoral vein was catheterized with a 6F side-armed sheath, followed by inserting a multi-hole pigtail catheter through the sheath to the inferior vena cava. A standard lead II electrocardiogram was also monitored continuously. Core temperature was maintained at 37 degrees Celsius using a heating pad.

A standard No. 19 jelco gauge, which was connected to a short extension tube with stopcock, was inserted into a left foreleg vein. The sonicated contrast agent was injected either through the stopcock into the peripheral vein or through the pigtail catheter into the inferior vena cava.

(b) Contrast Agent Preparation: The contrast agent was prepared according the procedure described in Example 1 by mixing commercially available human albumin, glucose, and distilled water to make a 10 ml solution. Then 0.6 ml of glycerin was added to make the final echo contrast agent solution of this invention. A Heat System sonicator (Model M-375) with a 0.5-inch (1.27 cm) diameter horn was used to generate microbubbles by the inserting the tip of the sonicated horn into the echo contrast solution and sonicating the solution for 70 seconds.

Figure 3A:
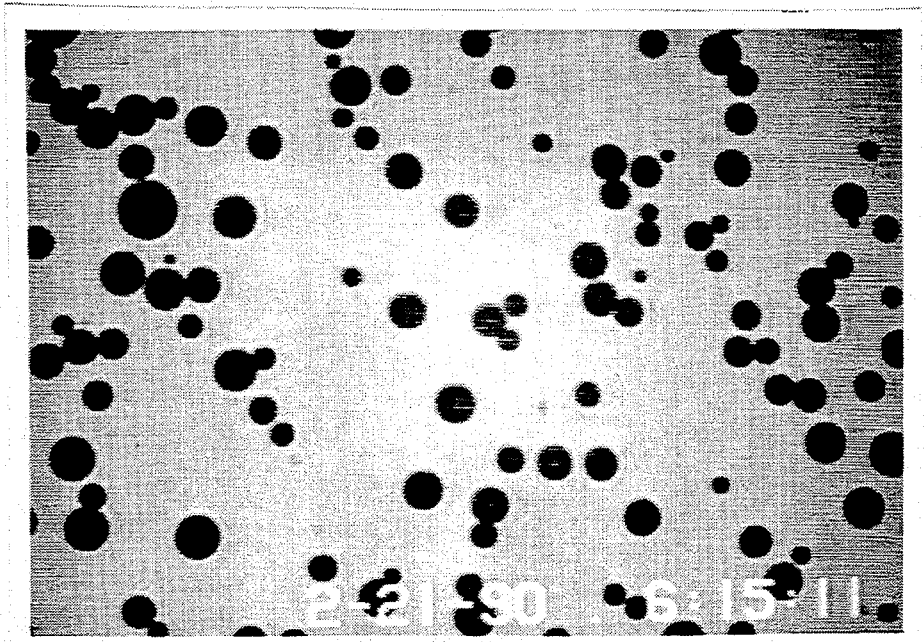
FIGS. 3a and 3b are the microscopic pictures (×400) of the microbubbles generated from the echo contrast agent of this invention and the red blood cells, respectively.
Figure 3B:
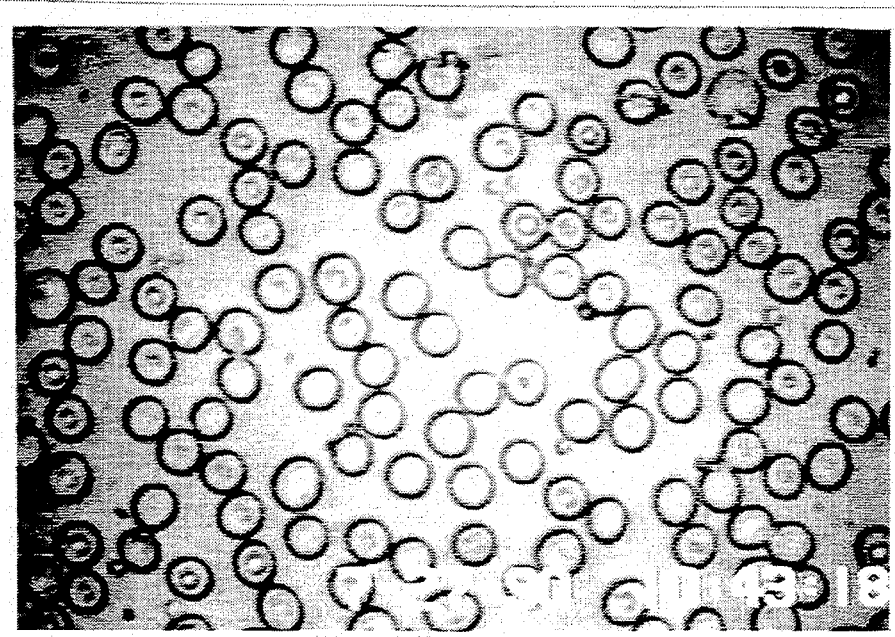

After sonification, one drop of the solution was sampled from the middle layer and quickly placed on a microscope slide and then covered with a coverslip. The images of the microbubbles in different regions were recorded into a high quality videotape using a videocamera which can be played back subsequently for analysis. FIGS. 3a and 3b show the microscopic pictures ($\times 400$) of the microbubbles produced from this invention and of the red blood cells, respectively. It can be clearly seen that the mean diameter of the microbubbles from this invention is smaller than that of the red blood cells.

(c) Study Protocol: Multiple hand injections of 8 ml sonicated contrast solution of this invention were performed through the short extension tube and the jelco gauge into the foreleg vein, and through the pigtail catheter into the inferior vena cava. Each injection of the echo contrast agent was followed by a rapid flush with 10 ml normal saline solution. Thereafter, the electrocardiogram, blood pressure and heart rate were continuously monitored.

(d) Echocardiographic Study: Two-dimensional echocardiograms were performed using an Irex Meridian Echo machine with a 2.5 MHz transducer. The dogs on which the study was performed were placed on a special table with a cutout region corresponding to its heart area. A modified long axis view was obtained from a closed chest dog in the fight lateral decubitus position. The two-dimensional echocardiograms were first adjusted for optimal resolution and for good imaging quality during the baseline study. Once the gain setting was established, the total-gain, rejection, depth, transmit power and the time-gain compensations were kept constant throughout the study for each dog. All the contrast agent injections were recorded on high quality videotapes (FUJI VHS) for subsequent playback and off-line computer analysis.

Figure 4A:
FIGS. 4a and 4b show the selection of the region of interest (shown as rectangular cursor) in the center of the right ventricle and the left ventricle, respectively.
Figure 4B:
Figure 4C:
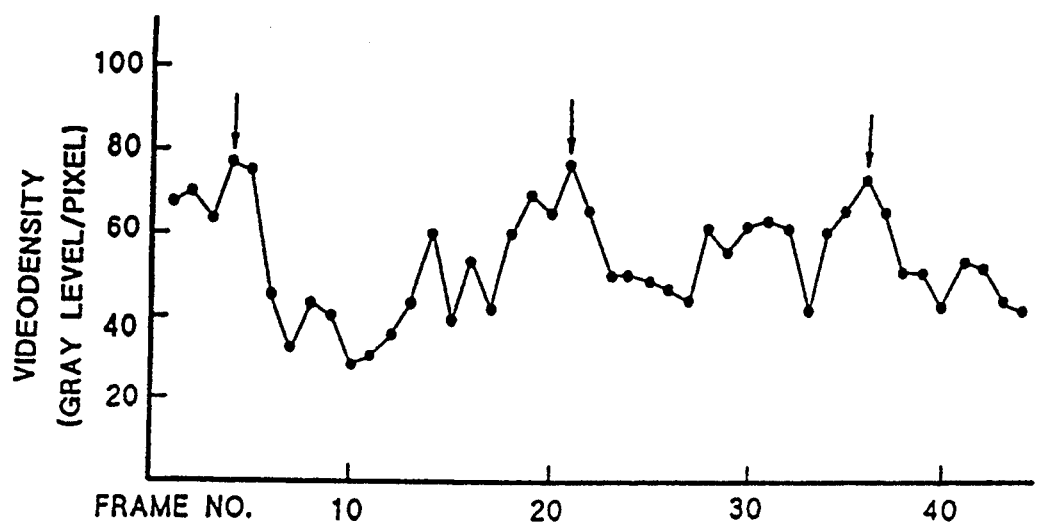
FIGS. 4c and 4d show the videodensity of the right ventricle and the left ventricle, respectively, during three cardiac cycles.
Figure 4D:
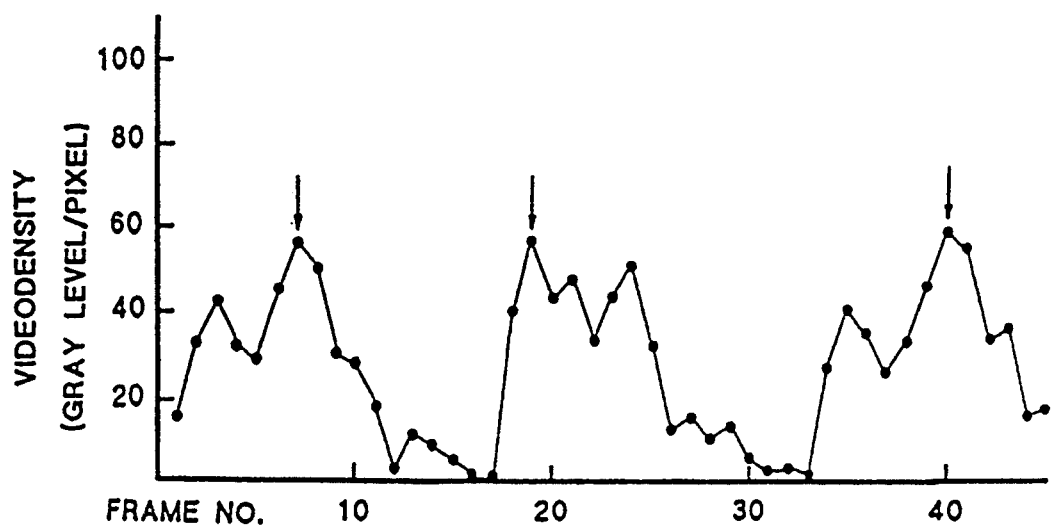
Figure 5:
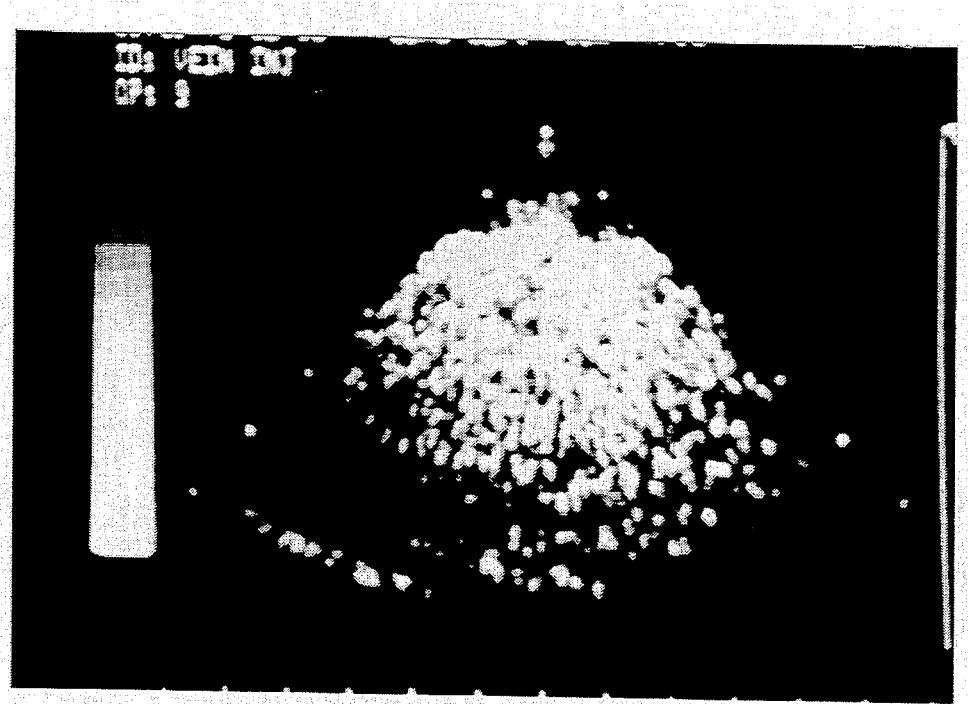
FIG. 5 shows an echocardiagram having excessive right ventricular echo with lateral shadowing which may affect the videodensity measurement.
Figure 6A:
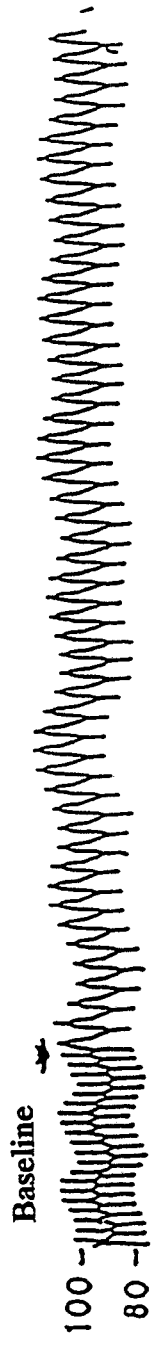
FIG. 6 shows the plot of blood pressure vs. time for two cases of peripheral venous injections (top two curves) and two cases of inferior vena cava injections (bottom two curves). Arrows indicate the injection of the echo contrast agent of this invention. Very slight increase in blood pressure was observed in some cases, but it soon returned to the baseline.
Figure 6B:
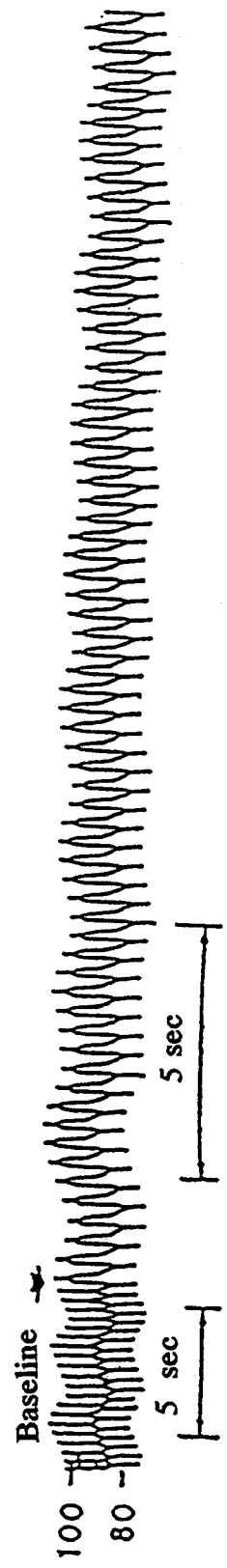
Figure 6C:
Figure 6D:
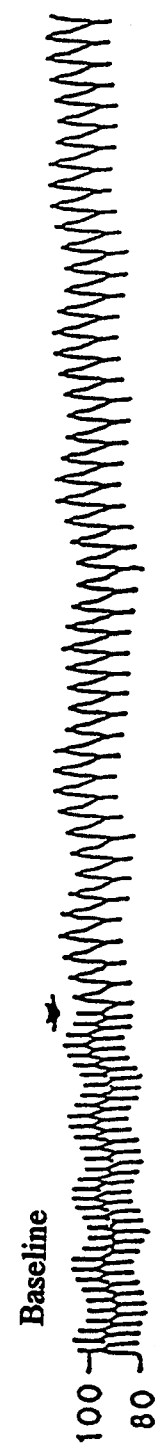

(e) Videodensitometric Analysis: were analyzed off-line using an image digitizing system which comprises a multifunctioning VHS videocassette recorder (Panasonic model AG-6300), a high resolution color monitor with an RGB signal output (Barco), a Time Base Corrector and a computer system. The computer system is capable of digitizing a full region of analog video data into a digital image having $512 \times 512$ pixels, each pixel is represented by one of 256 gray levels from 0 to 255. A region of interest at the center of the right ventricle and the left ventricle without other cardiac structures such as endocardium, valvular leaflets and chordae was selected. The videodensity of such a region of interest was then determined by this image digitizing system. The background videodensity of the right ventricle and the left ventricle was evaluated in 10 frames and the mean gray level was obtained. The videodensities of the same regions at the center of both the right and the left ventricles were measured in all frames for three consecutive cardiac cycles. The three consecutive cardiac cycles consist of the cardiac cycle having peak ventricular contrast enhancement and the preceding and the subsequent cycles. FIGS. 4a and 4b show, respectively, the region of interest that had been selected at the center of the right and the left ventricles. FIGS. 4c and 4d show and the videodensity of the fight ventricle and the left ventricle, respectively, during the three cardiac cycles. In FIGS. 4c and 4d, the peak videodensity (pointed to by an arrow) of each cardiac cycle was determined and the mean value was calculated. The peak videodensities of the right and the left ventricles, after subtracting the background videodensity of each ventricle, were obtained respectively. The ratio of the peak videodensity of the left ventricle to that of the right ventricle was further calculated for each injection. A sample volume of 64 pixels was chosen within the region of interest for all the analyses. FIG. 5 shows a case in which excessive right ventricular echo with lateral shadowing was observed. This usually occurred in the first two to three cycles at the beginning of the contrast echo. Since such excessive echo may affect the videodensity measurement, these frames were excluded, and only the cardiac cycles with peak right ventricular contrast without shadowing were selected for analysis.

(f) Statistical Analysis:

The Wilcoxon rank sum test was used to compare videodensity, the pulmonary transit time and the left ventricular persistence time from peripheral venous injection versus inferior vena cava injection. Statistical significance is defined as $p < 0.05$.

The "left ventricular contrast persistence time" is defined as the total amount of time in seconds during which the echo contrast was detectable within the region of interest in the left ventricle. It was measured from the time at which echo contrast began to appear, to the time at which the videodensity decreased to the baseline intensity.

The "pulmonary transit time", also in seconds, is defined as the total amount of time measured from the arrival time of the contrast echo in the right ventricle to the arrival time of the contrast echo in the left ventricle.

(2) Results:

(a) Microbubble diameter:

As shown in FIGS. 3a and 3b, respectively, the microbubble diameter ranged from 1 to 9 microns (mean 5.0±2.3 microns), compared to 6 to 9 microns for red blood cells (mean 7.1±0.9 microns).

(b) Side Effects:

All dogs tolerated the peripheral venous and inferior vena cava injections of the echo contrast agent of this invention. There was no arrhythmia or ST-T change in the electrocardiogram. Also no significant change in heart rate was noted before and after injection of the echo contrast agent of this invention. FIG. 6 shows that slight increase in blood pressure after injection was noted in all dogs, but it soon returned to the baseline value. The increased systolic blood pressure (112.7±9.5 mm Hg) was statistically insignificant compared to the baseline blood pressure (108.5±9.4 mm Hg). The echocardiograms revealed no regional wall motion abnormalities for all the cases studied.

Figure 7A:
FIG. 7a is an echocardiogram recorded from a dog before the injection of the echo contrast agent of this invention.
Figure 7B:
FIGS. 7b and 7c are the right ventricle and left ventricle echocardiograms, respectively recorded from the same dog as in FIG. 7a, after the injection of the echo contrast agent of this invention.
Figure 7C:

(c) Right ventricular and left ventricular contrast:

All injections produced contrast echo in the right ventricle. Excessive right ventricular echo in the initial 2-3 cardiac cycles after the injections of the echo contrast of this invention may result in substantial shadowing which was observed in all injections. FIGS. 7a shows the echocardiogram in a dog before the injection of the echo contrast agent. FIGS. 7b and 7c demonstrated the echocardiograms of the fight ventricle and the left ventricle, respectively, after the injection of the echo contrast agent. Dense echo contrast in the left ventricle was noted which indicated a great amount of contrast agent has traversed the lungs. In the peripheral venous injection cases, the mean fight ventricular and the left ventricular background videodensity were 0.63±35 and 0.13±0.16 gray level per pixel, respectively. In the left ventricular videodensity curve, the peak videodensity occurred not only in early diastole but also in atrial systole. In FIGS. 4c and 4b, which show the videodensity curve of the right ventricle and the left ventricle, respectively, there were two top points in each cardiac cycle. In the first and third cycles, the peak videodensity occurred at atrial systole, whereas in the middle cycle, it occurred at early diastole. Meanwhile, the videodensity tended to decrease in systole.

Figure 8:
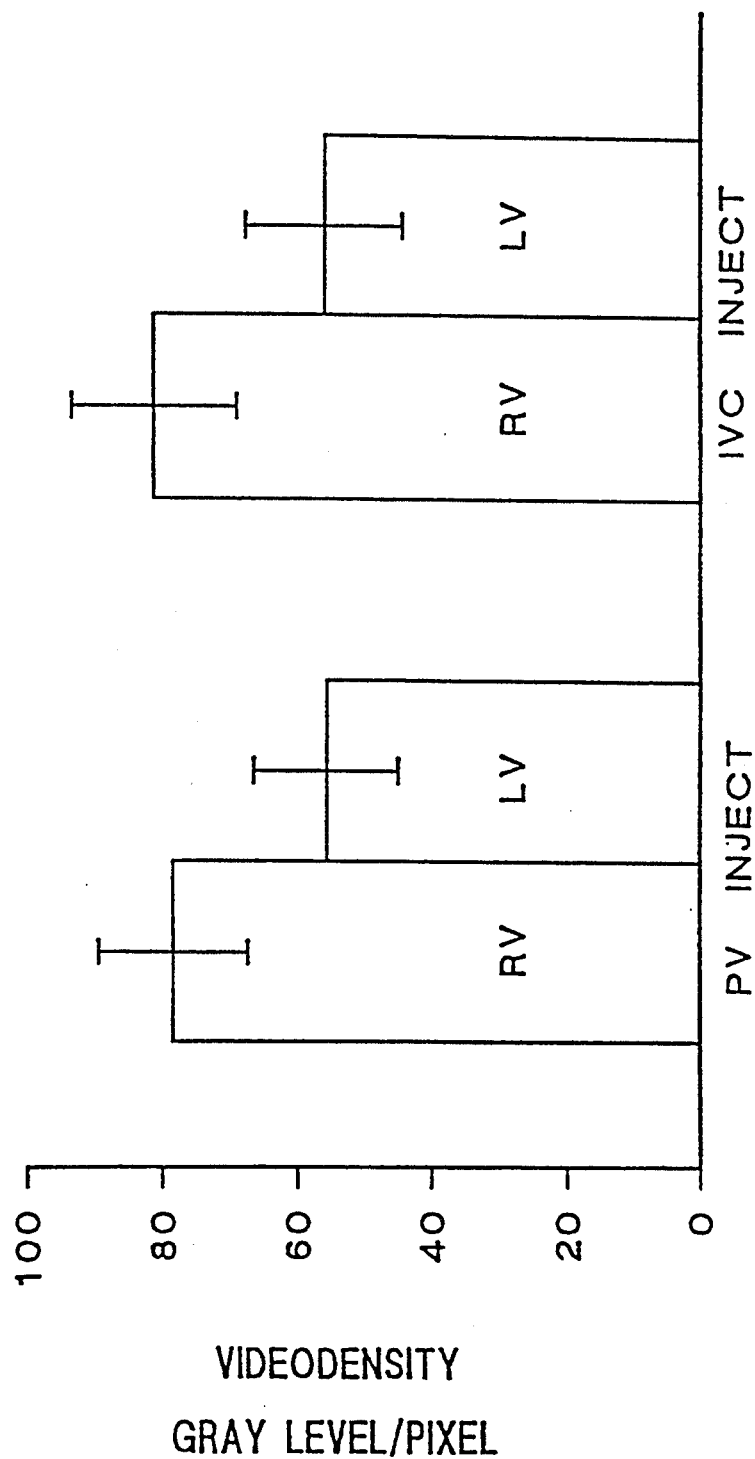
FIG. 8 is a bar chart showing the peak videodensity of the left and right ventricles after the peripheral venous and inferior vena cava injections of the echo contrast agent of this invention.

In the peripheral injection cases, after subtracting the background density, the mean peak videodensity for the fight ventricle was 78.4±11.1 gray level per pixel. Thirty-four (85%) of the 40 peripheral venous injections resulted in a left ventricular contrast having a mean peak left ventricular videodensity of 55.6±10.73 gray level per pixel. The peak left ventricular videodensity to peak right ventricular videodensity (LV/RV) in individual injections ranged from 0.42 to 0.90 (mean 0.68±0.15). On comparison, after subtracting the baseline videodensity, the inferior vena cava injection produced a left ventricular contrast with a mean peak right ventricular videodensity of 81.22±12.24 gray level per pixel. FIG. 8 shows that the peak left ventricular videodensity was 56.04±11.68 gray level per pixel. This is 65% as bright as that from the right ventricle.

(d) Pulmonary transit time and left ventricular persistence time:

In peripheral venous injection, the pulmonary transit times ranged from 2.83 to 4.48 (mean 4.05±0.53) seconds, and the left ventricular contrast persistence times ranges from 12.0 to 14.5 (mean 13.67±4.28) seconds. Compared to those from inferior vena cava injections, for which the mean pulmonary transit time was 3.93±0.47 seconds, p=NS, and the mean left ventricular contrast persistent time was 11.65±4.66 seconds, p=NS, there was no difference, statistically speaking, from the peripheral venous injections.

Table 1 summarizes study results after injection of the echo contrast agent of this invention.

Although the best mode contemplated for carrying out the present invention has been herein shown and described, it will be apparent that modification and variation may be made without departing from what is regarded as the subject matter of the invention.

TABLE 1

|  | Peripheral venous injection | Inferior vena cava injection |
|---|---|---|
| Pulmonary transit time (seconds) | 4.05 ± 0.53 | 3.93 ± 0.47 |
| Left ventricular persistence time (seconds) | 13.67 ± 4.28 | 11.65 ± 4.66 |
| Right ventricular background videodensity* | 0.63 ± 0.35 | 1.00 ± 0.90 |
| Left ventricular background videodensity* | 0.13 ± 0.16 | 0.13 ± 0.18 |
| Right ventricular peak videodensity* | 78.40 ± 11.10 | 81.22 ± 12.24 |
| Left ventricular peak videodensity* | 55.66 ± 10.73 | 56.04 ± 11.68 |
| Left ventricular/right ventricular videodensity* ratio | 0.68 ± 0.15 | 0.65 ± 0.18 |

*The unit of videodensity is gray level per pixel.

What is claimed is:

1. An improved echo contrast agent for use in echocardiography to opacify left ventricle, comprising:
    (a) an aqueous albumin-glucose solution containing 0.40 to 0.60 grams of albumin and 4.0 to 10.0 grams of glucose per 10 ml of said aqueous albumin-glucose solution;
    (b) glycerin having a volume ratio between said glycerin and said aqueous albumin-glucose solution of no less than 0.050; and
    (c) a plurality of microbubbles having diameters ranging from approximately 1 to 9 microns.

2. The echo contrast agent of claim 1 wherein said aqueous albumin-glucose solution contains 0.5 grams of albumin and 5.0 grams of glucose per 10.0 ml of said aqueous albumin-glucose solution and said volume ratio between said glycerin and said aqueous albumin-glucose solution is 0.060.

3. The echo contrast agent of claim 1 which contains a plurality of gas-in-liquid microbubbles that were generated through sonication.

4. The echo contrast agent of claim 3 wherein said microbubbles have a mean diameter of approximately between 4.0 and 5.0 microns.

5. The echo contrast agent of claim 3 wherein said microbubbles can be introduced into a body through peripheral venous injection and are capable of traversing the pulmonary circulation of said body without losing a significant portion thereof.

6. The echo contrast agent of claim 3 wherein said microbubbles can be introduced into a body through inferior vena cava injection and are capable of traversing the pulmonary circulation of said body without losing a significant portion thereof.

7. The echo contrast agent of claim 3 wherein said microbubbles are generated with an ultrasonic sonication device which generates a sound wave having frequencies in the range between 10-30 KHz.

* * * * *